(12) United States Patent
Shimotoyodome et al.

(10) Patent No.: US 8,071,572 B2
(45) Date of Patent: Dec. 6, 2011

(54) PREVENTIVE/REMEDY FOR OBESITY

(75) Inventors: Akira Shimotoyodome, Tochigi (JP); Junko Suzuki, Tochigi (JP); Noriyuki Yajima, Tochigi (JP); Takatoshi Murase, Tochigi (JP); Ichirou Tokimitsu, Tokyo (JP)

(73) Assignee: Kao Corporation, Tokyo (JP)

( * ) Notice: Subject to any disclaimer, the term of this patent is extended or adjusted under 35 U.S.C. 154(b) by 985 days.

(21) Appl. No.: 10/547,776

(22) PCT Filed: Mar. 8, 2004

(86) PCT No.: PCT/JP2004/002948
§ 371 (c)(1),
(2), (4) Date: Sep. 6, 2005

(87) PCT Pub. No.: WO2004/080470
PCT Pub. Date: Sep. 23, 2004

(65) Prior Publication Data
US 2006/0178343 A1    Aug. 10, 2006

(30) Foreign Application Priority Data
Mar. 11, 2003 (JP) .................................. 2003-065382

(51) Int. Cl.
A61K 31/718 (2006.01)
C08B 35/02 (2006.01)
C08B 35/04 (2006.01)
C08B 33/02 (2006.01)
C08B 33/04 (2006.01)
C08B 31/06 (2006.01)
C08B 31/12 (2006.01)

(52) U.S. Cl. ........................... 514/60; 536/106; 536/111

(58) Field of Classification Search ........................ None
See application file for complete search history.

(56) References Cited

U.S. PATENT DOCUMENTS

| | | | | |
|---|---|---|---|---|
| 3,577,407 A | * | 5/1971 | Hjermstad | 536/111 |
| 4,009,291 A | * | 2/1977 | Mitchell et al. | 426/548 |
| 4,865,867 A | * | 9/1989 | Platt et al. | 426/603 |
| 5,110,612 A | * | 5/1992 | Quarles et al. | 426/548 |
| 6,488,980 B1 | * | 12/2002 | Jeffcoat et al. | 426/661 |
| 6,541,060 B2 | * | 4/2003 | Jeffcoat et al. | 426/578 |

FOREIGN PATENT DOCUMENTS

| | | |
|---|---|---|
| JP | 3-290170 | 12/1991 |
| JP | 5-186356 | 7/1993 |
| JP | 05-504484 | 7/1993 |
| JP | 2002-010753 | 1/2002 |
| JP | 2002-051735 | 2/2002 |
| JP | 2002-503959 | 2/2002 |
| WO | 91/01092 | 2/1991 |
| WO | 98/54973 | 12/1998 |
| WO | 00/19841 | 4/2000 |

OTHER PUBLICATIONS

Merriam-Webster's Collegiate Dictionary, Tenth Edition, Published 1998 by Merriam-Webster, Inc. p. 924.*
Ebihara et al., "Hydroxypropyl-Modified Potato Starch Increases Fecal Bile Acid Excretion in Rats" Journal of Nutrition (1998) vol. 28, No. 5, pp. 848-854.*
The Merck Manual of Diagnosis and Therapy, Seventeenth Edition. Published 1999 by Merck Research Laboratories. edited by Beers and Berkow, pp. 58-62 and 165-169.*
Lewis et al., "Disordered Fat Storage and Mobilization in the Pathogenesis of Insulin Resistance and Type 2 Diabetes" Endocrine Reviews (2002) vol. 23 pp. 201-229.*
Buttolph et al., "Modified Food Starch in Hamster and Rats: Effects of Magnesium and Calcium" Trace Element Metabolism in Man and Animals (1982) pp. 158-161.*
T. A. Anderson et al., "Effect of Waxy Corn Starch Modification on Growth, Serum Biochemical Values and Body Composition of Pitman-Moore Miniature Pigs", Fd Cosmet. Toxicol., vol. 11, pp. 747-754, 1973.
John H. Cummings, "Nutritional implications of dietary fiber", The American Journal of Clinical Nutrition, vol. 31, Suppl. 10, pp. S21-S29 1978.
Shigeru Wakabayashi, "The effects of indigestible dextrin on sugar tolerance: I. studies on digestion-absorption and sugar tolerance", Endocrine Journal, vol. 68, No. 6, pp. 623-635 1992.
Kay M. Behall et al., "Diets containing high amylose vs amylopectin starch: effects on metabolic variables in human subjects[1-3]", Am. J. Clin. Nutr., vol. 49, No. 2, pp. 337-344 1989.
D. Molnar et al., "The effect of unprocessed wheat bran on blood glucose and plasma immunoreactive insulin levels during oral glucose tolerance test in obese children", Acta Paediatrica Hungarica, vol. 26, No. 1, pp. 75-77 1985.
S. Wakabayashi, et al., "Effects of indigestible dextrin on glucose tolerance in rats", Journal of Endocrinology, vol. 144, No. 3, pp. 533-538 1995.
Kaori Ono et al., "Properties of hydroxypropylated wheat starches", Journal of Home Economics of Japan, vol. 49, No. 9, pp. 985-992 1998.
AP De Groot, et al., Fd Cosmet. Toxicol., vol. 12, pp. 651-663, Pergamon Press, printed in Great Britain (1974).
HP Til, et al., Fd Chem. Toxic., vol. 24, No. 8, pp. 825-834, printed in Great Britain (1986).
T. Kishida, et al., The Journal of Nutrition, vol. 131, No. 2, pp. 294-300 (Feb. 2001).

* cited by examiner

*Primary Examiner* — Eric S Olson
(74) *Attorney, Agent, or Firm* — Oblon, Spivak, McClelland, Maier & Neustadt, L.L.P.

(57) ABSTRACT

The present invention relates to a preventive/remedy for obesity, which has a hydroxypropylated starch as its active ingredient.

Provided are materials for foods, drugs, etc. which can exhibit an effect of preventing/lessening the onset of various lifestyle related diseases, for example, an effect of preventing/ameliorating obesity, or preventing/ameliorating hyperlipidemia; have a high safety and a wide application range; and rarely damage their texture.

14 Claims, No Drawings

PREVENTIVE/REMEDY FOR OBESITY

FIELD OF THE INVENTION

The present invention relates to a material having an effect of preventing/ameliorating various lifestyle related diseases such as obesity and diabetes, which can be used for food or medicine.

BACKGROUND OF THE INVENTION

In recent years, lifestyle related diseases including obesity and diabetes are increasing owing to the world-wide tendency to excessive energy intake (increase in the intake of fats or sucrose) and insufficient exercise. Considering such a social background, a measure for preventing or ameliorating obesity or diabetes is very important.

One of the methods proposed commonly by nutritionists in order to prevent or ameliorate obesity or diabetes is intake of a low calorie diet or low fat diet. It has recently been reported that water insoluble food fiber such as wheat bran, water soluble food fiber such as indigestible dextrin, and digestion resistant starch such as high amylose starch have a lipid excretion accelerating action (Am. J. Clin. Nutr., 31 (10 Suppl), S21-S29(1978)), a sugar absorption inhibitory action (Endocrine Journal, 68(6), 623-35(1992)), and a blood neutral fat level lowering action (Am. J. Clin. Nutr. 49(2), 337-44(1989)), or a glucose tolerance improving action (Acta Paediatr Hung 1985 26(1):75-7, J Endocrinol 1995 144(3): 533-8, Am J Clin Nutr 1989 49(2):337-44), respectively. It is suggested that they are therefore effective for the prevention/amelioration of obesity, or prevention/amelioration of diabetes.

A drastic rise in the after-meal blood lipid level is presumed to accelerate accumulation of fats, so that suppression of after-meal hyperlipidemia (a rise in blood triglyceride level) is also a very important approach for the prevention/amelioration of obesity. In recent years, xanthan gum and propylene glycol alginate (JP-A-1993-186356), and chitosan (JP-A-1991-29017) have been reported as a safe and effective lipid absorption inhibitor.

The above-described low calorie diet or low fat diet temporarily brings about an effect on weight decrease, but after intake of it for a prolonged time, it comes to be refused because of a monotonous taste of the food constituting such a diet. It is therefore difficult to continue consuming such a diet. The above-described conventional food materials such as water insoluble food fiber, water soluble food fiber and digestion resistant starch do not exhibit the above-described physiological actions until they are administered for a long period of time at a high dosage. Even if they exhibit these physiological actions, their effect for inhibiting obesity has not yet been confirmed. Moreover, when food or beverage is prepared using them, the original texture of the food or beverage such as appearance, taste, touch or smoothness tends to be damaged and it is therefore difficult to incorporate a sufficient amount of them in food. This leads to problems such as limited application range and difficulty in intake of such food or beverage for a long period of time.

A hydroxypropylated starch is known to have high transparency, excellent film forming property, and high low-temperature storage stability and lyophilization/thawing stability. And use of it for food is approved by FDA in USA (Journal of Home Economics of Japan, 49(9), 985-992(1998)).

It is however unknown that hydroxypropylated starches have an effect of preventing/lessening the onset of lifestyle related diseases such as obesity and diabetes.

DISCLOSURE OF THE INVENTION

In one aspect of the present invention, there are thus provided a preventive/remedy for obesity, visceral fat accumulation inhibitor, blood sugar level rise inhibitor, blood triglyceride level rise inhibitor and preventive/remedy for diabetes, each containing a hydroxypropylated starch as its active ingredient.

In another aspect of the present invention, there is also provided use of a hydroxypropylated starch for the preparation of a preventive/remedy for obesity, visceral fat accumulation inhibitor, blood sugar level rise inhibitor, blood triglyceride level rise inhibitor and preventive/remedy for diabetes.

In a further aspect of the present invention, there are also provided a method of preventing/ameliorating obesity, a method of inhibiting visceral fat accumulation, a method of inhibiting a rise in a blood sugar level, a method of inhibiting a rise in a blood triglyceride level and a method of preventing/ameliorating diabetes.

MODE FOR CARRYING OUT THE INVENTION

The present invention provides a material for food, medicine, pet food and the like which exhibits effects of preventing/lessening the onset of various lifestyle related diseases, for example, effects of preventing/ameliorating obesity, preventing/ameliorating hyperlipidemia and the like, has a high safety and can be used widely, and scarcely impairs the texture of a substance to which the material has been added.

The present inventors have searched for materials having physical properties different from those of the conventional food fibers typified by indigestible starch, cellulose, and indigestible dextrin, and at the same time having an effect of inhibiting/ameliorating the progress of obesity or diabetes. As a result, they have found that a hydroxypropylated starch exhibits various physiological actions at a low dose, and is useful as a material for food, medicine or pet food exhibiting an effect of preventing/ameliorating lifestyle related diseases such as obesity and diabetes.

The preventive/remedy for obesity and the like according to the present invention has an effect of preventing/lessening the onset of various lifestyle related diseases, for example, an effect of preventing/ameliorating obesity, preventing/ameliorating hyperlipidemia, preventing heart diseases such as heart failure, preventing thrombosis, preventing colon cancer or rectal cancer and the like, so that it is useful as food, medicine, pet food or the like. In particular, since a hydroxypropylated starch serving as its active ingredient uses starch as its raw material, it is safe to the human body, its application range to foods and beverages is wide because it can be gelatinized easily, and even if added to a specified health food, it hardly damages the original texture of the food.

The hydroxypropylated starch to be used in the present invention can be obtained by hydroxypropylating starch or processed starch in a conventional manner. More specifically, it is obtainable by reacting propylene oxide with starch.

Commercially available products such as "National FRIGEX" (tapioca-based product of National Starch and Chemical), "National 1658" (corn-based product of National Starch and Chemical), "THERMFLO" (waxy-corn-based product of National Starch and Chemical) and "THERMTEX" (waxy-corn-based product of National Starch and Chemical) can also be used.

Examples of the raw material starch include waxy corn starch, corn starch, wheat starch, rice starch, sticky-rice starch, potato starch, ocarina starch, tapioca starch, and sago starch. Starch having an amylopectin content of 70 wt. % or greater, preferably from 75 to 100 wt. %, more preferably from 90 to 100 wt. % is preferred, because owing to high transparency of its solution, addition of it to a beverage does not damage the appearance thereof, and it widens the application range. Of these, waxy corn starch and tapioca starch are preferred as raw material starch.

The term "hydroxypropylated starch" as used herein also includes hydroxypropylated starch available by using another processing treatment in combination. Examples of the processing treatment usable in combination include esterification with acetic acid, octenylsuccinic acid, phosphoric acid or the like, etherification other than hydroxypropylation such as carboxymethyl etherification, crosslink treatment with an ordinarily employed crosslinking agent such as trimetaphosphate, hexametaphosphate, phosphorus oxychloride, adipic acid, epichlorohydrin or the like, oxidation treatment, acid treatment, bleaching treatment, moist heat treatment, heat treatment, and enzyme treatment. One or at least two of them may be used in combination. Of these, esterification is preferred, with phosphorylation, especially crosslink treatment with phosphoric acid is more preferred. Phosphorylation is performed so that a bound phosphorus content falls within a range of from 0.0001 to 2%, preferably from 0.0001 to 0.5%, more preferably from 0.0001 to 0.2% from the viewpoint of texture and the like.

With regards to the degree of hydroxypropylation, the degree of substitution (the number of hydroxypropyl groups per residue of anhydrous glucose in starch) is preferably from 0.001 to 1, more preferably from 0.05 to 0.5, still more preferably from 0.1 to 0.3.

The above-described hydroxypropylated starch can be prepared from starch in high purity at a relatively low cost only by simple steps. It has a high safety and compared with the conventional food fiber or indigestible starch, various foods and beverages, medicines, pet foods or the like added with it brings no discomfort in texture. In addition to these advantages, it has excellent freezing resistance so that it is free from deterioration by thawing.

First, the hydroxypropylated starch has an obesity inhibiting action and causes a significant decrease in weight and visceral fat level as described later in Examples. It is therefore effective for the prevention of hyperlipidemia attributable to obesity, prevention of heart diseases such as heart failure, prevention of thrombosis, prevention of hypertension, and the like. Secondly, it has an action of suppressing after-meal hyperlipidemia, more specifically, a rise in a blood triglyceride level after meal. Thirdly, it has an action of suppressing after-meal hyperglycemia, that is, a drastic rise in a blood sugar level after meal and at the same time, suppressing a rise in a steady state blood sugar level. It is therefore effective for the prevention of diabetes or various complications associated therewith such as cataract, periodontal disease, diabetic nephropathy, nephropathy and neuropathy.

The hydroxypropylated starch according to the present invention therefore becomes a material for foods or medicines for humans or animals as a preventive/remedy for obesity, blood triglyceride level rise inhibitor, blood sugar level rise inhibitor, or preventive/remedy for diabetes (which will hereinafter be called "obesity preventive/remedy or the like" simply).

As the obesity preventive/remedy or the like according to the present invention, at least one hydroxypropylated starch can be administered singly to humans or animals, or a mixture of it in food or beverage, medicine or pet food can be given. The food in which the hydroxypropylated starch can be mixed is, for example, beauty diet having a physiological function as such as body fat accumulation suppression or blood sugar level rise suppression, diet for patients, or specified health food. When it is used as a medicine, it can be provided as orally administrable solid preparations such as tablets and granules or orally administrable liquid preparations such as liquids for internal use and syrups.

The orally administrable solid preparations can be obtained by adding to the hydroxypropylated starch of the present invention, an excipient and if necessary, a binder, a disintegrant, a lubricant, a colorant, a taste corrigent, an odor improving agent or the like and then forming the resulting mixture into tablets, coated tables, granules, powders, capsules or the like in a conventional manner. The orally administrable liquid preparations can be obtained by adding a taste corrigent, a buffer, a stabilizer, a taste corrigent and the like and forming the mixture into a liquid for internal use, syrup or elixir in a conventional manner.

The amount of the hydroxypropylated starch to be mixed in each preparation is usually from 5 to 100 wt. %, preferably from 20 to 100 wt. %, more preferably from 30 to 100 wt. %.

The daily administration amount (effective intake) of the obesity preventive/remedy or the like of the present invention is preferably from 0.01 g/kg weight or greater, more preferably 0.1 g/kg weight or greater, even more preferably 0.4 g/kg weight or greater.

EXAMPLES

Test 1: Obesity Inhibitory Action • Blood Sugar Level Rise Inhibitory Action of Hydroxypropylated Starch Tapioca starch and waxy corn starch were purchased from National Starch and Chemical. Commercially available "National FRIGEX" (tapioca-based product of National Starch and Chemical), "THERMFLO" (degree of hydroxypropylation (D.S.)=0.154, degree of phosphorylation (bound phosphorus content)=0.004%, waxy-corn-based product of National Starch and Chemical) were used as the hydroxypropylated starch.

The above-described starch was suspended in distilled water to give its content of 50 wt. %. The resulting suspension was autoclaved (moist heat treatment) at 120° C. for 15 minutes, followed by lyophilization, whereby a gelatinized starch to be tested was prepared.

Mice (C57BL/6J male, 6 week old) were divided into groups, each group consisting of 10 mice, and fed with diets prepared according to the composition as shown in Table 1 by using various gelatinized starches. After feeding for 24 weeks, blood was collected from mice. They were then sacrificed and blood sugar level and visceral fat weight were measured. Weights of the mice after feeding for 10 weeks and 23 weeks and visceral fat weight and blood sugar level after breeding for 24 weeks are shown in Table 2.

TABLE 1

| Composition of feed (wt. %) | | |
|---|---|---|
| | Low-fat feed | Test feed (high fat · high sucrose) |
| Gelatinized test starch | 0% | 5% |
| Gelatinized potato starch | 66.5% | 23.5% |
| Sucrose | 0% | 13% |
| Lipid | 5% | 30% |
| Casein | 20% | 20% |

TABLE 1-continued

Composition of feed (wt. %)

|  | Low-fat feed | Test feed (high fat · high sucrose) |
|---|---|---|
| Cellulose | 4% | 4% |
| Mineral mixture | 3.5% | 3.5% |
| Vitamin mixture | 1% | 1% |

TABLE 2

Weight and visceral fat weight of mouse

| | Base | Hydroxypropylation | Crosslink with phosphoric acid | Average weight (g) after 10 weeks | Average weight (g) after 23 weeks | Visceral fat weight (g) | Blood sugar level (mg/dL) |
|---|---|---|---|---|---|---|---|
| Low-fat feed | — | — | — | 23.9 | 27.2 | 1.03 | 196.5 |
| Tapioca starch | tapioca | x | x | 31.1 | 34.4 | 2.67 | 235.3 |
| Hydroxypropylated starch*[1] | Tapioca | ○ | ○ | 29.1* | 30.9*** | 1.59***** | 211.1 |
| Waxy corn starch | Waxy corn | x | x | 30.2 | 32.6 | 1.91 | 218.9 |
| Hydroxypropylated starch*[2] | Waxy corn | ○ | ○ | 28.7** | 31.3 | 1.53* | 194.2 |

*[1]: "National FRIGEX",
*[2]: "THERMFLO"
○ and x mean that the processed starch was subjected to chemical treatment or not.
○: chemically treated
x: not chemically treated
Statistical significance relative to corresponding raw material starch:
*: $P < 0.1$,
**: $P < 0.05$,
***: $P < 0.01$,
****: $P < 0.001$,
*****: $P < 0.0001$ From the results of Table 2, it has been found that the weight and visceral fat weight of the mice fed with the diet containing 5 wt. % of a hydroxypropylated starch (tapioca or waxy corn based starch) are significantly lower than those of the mice fed with the diet containing the corresponding raw material starch and this means that the hydroxypropylated starch has obesity inhibitory effect.

It has also been found that the steady state blood sugar level of the mice fed with the high fat diet containing 5% of tapioca or waxy corn starch is higher than that of the mice fed with the low fat diet. It has however been found that the steady state blood sugar level of the mice fed with the high fat diet containing 5% of hydroxypropylated tapioca or hydroxypropylated waxy corn starch is lower than that of the mice fed with the diet containing the corresponding raw material starch (tapioca or waxy corn based starch) and this means that the hydroxypropylated starch has a blood sugar level rise inhibitory effect.

Test 2: Obesity Inhibitory Action of Hydroxypropylated Starch

Tapioca starch and waxy corn starch were purchased from National Starch and Chemical. "National FRIGEX" (tapioca-based starch of National Starch and Chemical), "THERMFLO" (waxy-corn-based starch of National Starch and Chemical), or the above-described tapioca starch or waxy corn starch hydroxypropylated by the method as described in J. Nutr. 128(5), 845-54(1998) was employed as the hydroxypropylated starch. As the indigestible starch, commercially available "Fibose" (high amylose corn based product, Lot. 11785) was purchased from Nippon Starch Chemical Co., Ltd.

The above-described starch was suspended in distilled water to give its content of 50 wt. %. The resulting suspension was autoclaved (moist heat treatment) at 120° C. for 15 minutes, followed by lyophilization, whereby a gelatinized starch to be tested was prepared. Indigestible dextrin and cellulose were purchased from Matsutani Chemical Industry Co., Ltd. and Oriental Yeast Co., Ltd, respectively.

Mice (C57BL/6J male, 6 week old) were divided into groups, each group consisting of 10 mice, and fed for 13 weeks with diets prepared according to the composition as shown in Table 1 by using various gelatinized starches, indigestible dextrin and cellulose. Their weights were measured every week. The results are shown in Table 3.

TABLE 3

Weight of mouse after 13 weeks

| | Base | Hydroxy-propylation | Crosslink with phosphoric acid | Average weight (g) |
|---|---|---|---|---|
| Low fat feed | — | — | — | 27.2 |
| Tapioca starch | Tapioca | x | x | 32.0 |
| Hydroxypropylated tapioca starch | Tapioca | ○ | x | 30.0** |
| Hydroxypropylated starch*[1] | Tapioca | ○ | ○ | 29.5** |
| Waxy corn starch | Waxy corn | x | x | 31.6 |
| Hydroxypropylated waxy corn starch | Waxy corn | ○ | x | 29.3* |
| Hydroxypropylated starch*[2] | Waxy corn | ○ | ○ | 29.2** |

TABLE 3-continued

Weight of mouse after 13 weeks

|  | Base | Hydroxy-propylation | Crosslink with phosphoric acid | Average weight (g) |
|---|---|---|---|---|
| Indigestible starch*3 | High amylose corn | x | x | 31.5 |
| Indigestible dextrin | — | — | — | 31.5 |
| Cellulose | — | — | — | 33.3 |

*1: "National FRIGEX",
*2: "THERMFLO",
*3: "Fibose"
o and x mean that the processed starch was subjected to chemical treatment or not.
o: chemically treated
x: not chemically treated
Statistical significance relative to corresponding raw material starch:
P < 0.1,
**: P < 0.05

From the results of Table 3, it has been found that the weight of the mice fed with the diet containing 5 wt. % of the hydroxypropylated starch (tapioca-based or waxy-corn-based starch) is significantly lower than that of the mice fed with the diet containing a corresponding raw material starch, which means that the hydroxypropylated starch has obesity suppressing effect; while the indigestible starch (high-amylose-corn based starch), the indigestible dextrin which is a water soluble food fiber and cellulose which is a water insoluble food fiber have no obesity inhibiting effect.

Test 3: After-Meal Blood Triglyceride Level Rise Inhibitory Action of Hydroxypropylated Starch Tapioca starch and waxy corn starch were purchased from National Starch and Chemical. "National FRIGEX" (tapioca-based product of National Starch and Chemical), "THERMFLO" (waxy-corn-based product of National Starch and Chemical) were used as the hydroxypropylated starch. An indigestible starch, "Fibose" (high-amylose-corn-based starch, Lot. 11785) was purchased from Nippon Starch Chemical Co., Ltd.

The above-described starch was suspended in distilled water to give its content of 50 wt. %. The resulting suspension was autoclaved (moist heat treatment) at 120° C. for 15 minutes, whereby a gelatinized test starch was prepared.

SD rats (male, 8 week old) were divided into groups, each group consisting of 9 rats, and 3 mL of a lipid emulsion containing 0.15 g of a gelatinized starch, 0.2 g of a corn oil, 0.3 g of Na taurocholate and 0.052 g of bovine serum albumin was orally administered to them via a sonde. The blood was collected from their carotid artery 0, 30, 60, 120 and 240 minutes after administration and plasma was prepared. A triglyceride level in the plasma was measured using "Triglyceride Test Wako" (product of Wako Pure Chemical Industries). The results are shown in Table 4.

TABLE 4

Triglyceride level in rat plasma after administration of lipid emulsion

|  | Initial level | After 30 min | After 60 min | After 120 min | After 240 min |
|---|---|---|---|---|---|
| Tapioca starch | 43.2 | 49.0 | 80.3 | 68.8 | 44.0 |
| Hydroxypropylated starch *1 | 45.0 | 46.4 | 60.3** | 52.4* | 43.8 |
| Waxy corn starch | 44.8 | 48.0 | 74.7 | 69.4 | 45 |
| Hydroxypropylated starch *2 | 47.7 | 45.6 | 58.2** | 42.2* | 36.3 |
| Indigestible starch *3 | *50.0 | 48.6 | 61.2 | 88 | 56.7 |

*1: National FRIGEX
*2: THERMFLO
*3: Fibose
Statistical significance relative to corresponding raw material starch:
P < 0.1,
**: P < 0.05

From the results of Table 4, it has been found that the rats to which the lipid emulsion containing the hydroxypropylated starch (tapioca-based or waxy-corn-based starch) was orally administered show a significantly low rise in the plasma triglyceride level compared with the rats orally administered with the lipid emulsion containing the corresponding raw material starch or indigestible starch (Fibose) and this means that the hydroxypropylated starch has a blood triglyceride rise level inhibitory action.

Test 4: After-Meal Blood Sugar Level Rise Inhibitory Action of Hydroxypropylated Starch Tapioca starch, corn starch and waxy corn starch were purchased from National Starch and Chemical. "National FRIGEX" (tapioca-based starch of National Starch and Chemical), "National 1658" (corn-based starch of National Starch and Chemical), "THERMFLO" (waxy-corn-based starch of National Starch and Chemical), and THERMTEX (waxy-corn-based starch of National Starch and Chemical) were used as the hydroxypropylated starch. As the indigestible starch, high amylose corn starch and commercially available "Fibose" (high amylose corn based product, Lot. 11785) were purchased from Nippon Starch Chemical Co., Ltd.

The above-described starch was suspended in distilled water to give its content of 5 wt. %. The resulting suspension was autoclaved (moist heat treatment) at 120° C. for 15 minutes, and then allowed to cool down to room temperature.

The food fiber content of the starch after treatment was measured in accordance with the method of Akerberg Ak., et al. (J. Nutr. 128, 651-660(1998)).

The resulting starch suspension was orally administered to mice (C57BL/6J male, 6 week old, one group consisting of 6 mice) at a dose of 2 mg starch/g weight and 0, 30, 60 and 120 minutes after administration, the blood was collected from their caudal vein. The blood sugar level was measured using a simple blood sugar level measuring system ("Accu-Chek Comfort" of Roche Diagnostics).

The food fiber content of each test starch and the maximum blood sugar level and area under the curve of blood sugar level two hours after oral administration are shown in Table 5.

From the results of Table 5, it has been found that a rise in the blood sugar level of the mice orally administered with the hydroxypropylated starch (tapioca based or waxy corn based starch) is significantly low compared with that of the mice orally administered with the corresponding raw material starch, and in spite of a remarkably small food fiber content of the hydroxypropylated starch compared with the indigestible starch typified by high amylose corn starch, the hydroxypropylated starch has an after-meal blood sugar level rise inhibitory action comparable to these starches.

TABLE 5

| Name | Base | Hydroxypropylation | Crosslink with phosphoric acid | Food fiber content (%) | After-meal blood sugar level rise (maximum blood sugar level) | After-meal blood sugar level rise (area under the curve) |
|---|---|---|---|---|---|---|
| Tapioca starch | Tapioca | x | x | 1.0 | 283.3 | 256.1 |
| Hydroxypropylated starch*1 | Tapioca | o | o | 0.62 | 196.6* | 133.5* |
| Waxy corn starch | Waxy corn | x | x | 0.64 | 301.4 | 233.8 |
| Hydroxypropylated starch*2 | Waxy corn | o | o | 0.4 | 215.6* | 131.2* |
| Hydroxypropylated starch*4 | Waxy corn | o | o | 1.6 | 203.8* | 139.8* |
| Corn starch | Corn | x | x | 8.8 | 262.8 | 257.5 |
| Hydroxypropylated starch*5 | corn | o | o | 0.8 | 212.5* | 159.3* |
| High amylose corn starch | High amylose corn | x | x | 46.3 | 222.5* | 155.6* |
| Indigestible starch*3 | High amylose corn | x | x | 43.5 | 217* | 141.7* |

*1: "National FRIGEX",
*2: "THERMFLO",
*3: Fibose,
*4: "THERMTEX,
*5: "National 1658"
o and x mean that the processed starch is subjected to chemical treatment or not.
o: chemically treated
x: not chemically treated

The invention claimed is:

1. A method of ameliorating obesity, which comprises administering an obesity ameliorating effective amount to an obese subject in need thereof of a composition comprising from 5 to 100% by weight of a hydroxypropylated starch, wherein the hydroxypropylated starch has been crosslinked with phosphoric acid.

2. A method of decreasing visceral fat accumulation, which comprises administering a visceral fat decreasing effective amount to an obese subject in need thereof of a composition comprising from 5 to 100% by weight of a hydroxypropylated starch, wherein the hydroxypropylated starch has been crosslinked with phosphoric acid.

3. The method according to claim 1, wherein the hydroxypropylated starch is derived from a waxy corn starch or tapioca starch.

4. The method according to claim 1, wherein the hydroxypropylated starch is derived from a starch having an amylopectin content of 70 wt % or greater.

5. The method according to claim 4, wherein the amylopectin content is 90-100 wt %.

6. The method according to claim 1, wherein the hydroxypropylated starch has a degree of substitution of from 0.001 to 1.

7. The method according to claim 6, wherein the degree of substitution is from 0.1 to 0.3.

8. The method according to claim 1, wherein the hydroxypropylated starch is administered as part of a composition in which the hydroxypropylated starch replaces at least a portion of non-hydroxypropylated starch.

9. The method according to claim 2, wherein the hydroxypropylated starch is administered as part of a composition in which the hydroxypropylated starch replaces at least a portion of non-hydroxypropylated starch.

10. The method according to claim 2, wherein the hydroxypropylated starch is derived from a waxy corn starch or tapioca starch.

11. The method according to claim 2, wherein the hydroxypropylated starch is derived from a starch having an amylopectin content of 70 wt % or greater.

12. The method according to claim 11, wherein the amylopectin content is 90-100 wt %.

13. The method according to claim 2, wherein the hydroxypropylated starch has a degree of substitution of from 0.001 to 1.

14. The method according to 13, wherein the degree of substitution is from 0.1 to 0.3.

* * * * *